United States Patent [19]
Wiest et al.

[11] Patent Number: 4,998,914
[45] Date of Patent: Mar. 12, 1991

[54] PROCEDURE FOR THE PERFUSION OF CAVITIES IN OBJECTS AND DEVICE FOR EXECUTING THE PROCEDURE

[75] Inventors: Peter P. Wiest, Hessenallee 8, 1000 Berlin 19; Hubert Fuchs, Berlin, both of Fed. Rep. of Germany

[73] Assignee: Peter P. Wiest, Berlin, Fed. Rep. of Germany

[21] Appl. No.: 307,675

[22] Filed: Feb. 6, 1989

[30] Foreign Application Priority Data

Feb. 17, 1988 [DE] Fed. Rep. of Germany ....... 3805368

[51] Int. Cl.$^5$ ............................................. A61M 31/00
[52] U.S. Cl. .............................. 604/67; 128/DIG. 13; 604/153; 604/50
[58] Field of Search ..................... 604/67, 65, 66, 153, 604/49, 50, 59, 118, 246, 245; 128/DIG. 12, DIG. 13

[56] References Cited

U.S. PATENT DOCUMENTS

| | | | |
|---|---|---|---|
| 4,468,219 | 8/1984 | George et al. | 604/67 |
| 4,688,577 | 8/1987 | Bro | 604/50 |
| 4,743,228 | 5/1988 | Butterfield | 604/65 |
| 4,769,001 | 9/1988 | Prince | 128/DIG. 13 |
| 4,808,161 | 2/1989 | Kamen | 128/DIG. 12 |
| 4,826,482 | 5/1989 | Kamen | 604/67 |
| 4,846,792 | 7/1989 | Bobo, Jr. et al. | 128/DIG. 13 |
| 4,902,276 | 2/1990 | Zakko | 604/66 |
| 4,902,277 | 2/1990 | Mathies et al. | 604/67 |

FOREIGN PATENT DOCUMENTS 2530462  1/1984  France ............................... 604/67

Primary Examiner—Stephen C. Pellegrino
Assistant Examiner—Kathleen A. Daley
Attorney, Agent, or Firm—McGlew & Tuttle

[57] ABSTRACT

The invention relates to a procedure for the perfusion of body cavities with a fluid led from a dispenser reservoir 3 via a perfusion line 10 and a medical instrument 6. Pump 4 is connected with the perfusion line 10, a pressure sensor 5 is connected between pump 4 and medical instrument 6 to perfusion line 10, and an adjustment and measurement electronic system 12 is connected to pressure sensor 5 and pump 4.

To build up, maintain, and measure as precisely as possible a preselected and precisely determined pressure in the body cavity, according to the invention the adjustment and measurement electronic system 12 determines the actual pressure in body cavity 1 by evaluating the pressure $P_{IST}$ measured by pressure sensor 5, the volume flow V supplied by pump 4, and the conductance G of the perfusion line 9 between pressure sensor 5 and instrument 6 and conductance G of instrument 6, and the pressure $P_{SOLL}$ in body cavity 1 is maintained constant at preset level $P_{SOLL}$ by continuous adjustment of the output of pump 4 with due consideration for conductance G.

12 Claims, 3 Drawing Sheets

4,998,914

PROCEDURE FOR THE PERFUSION OF CAVITIES IN OBJECTS AND DEVICE FOR EXECUTING THE PROCEDURE

FIELD OF THE INVENTION

The invention relates to a procedure for the perfusion of body cavities with a fluid lead from a dispenser reservoir via a perfusion line and a medical instrument. A pump is connected to the perfusion line and a pressure sensor is connected to the perfusion line between the pump and the medical instrument. An electronic adjustment and measurement system is provided connected to the pressure sensor and the pump. The invention also pertains to a device for executing the procedure.

BACKGROUND OF THE INVENTION

A device for the perfusion of cavities with a liquid is already known from German reference 33 38 758 C 2. The pressure sensor used therein reports the actual value of the pressure inside the perfusion line into which the pressure sensor is inserted. A precise measurement of the pressure in the cavity itself cannot be made, because flow losses and hence pressure losses inside the perfusion line and inside the medical instrument distort the measured pressure value.

In order to precisely measure the pressure inside the cavity, the pressure sensor would have to be positioned at a distal end of the medical instrument, in particular an endoscope, such as, for example, an arthroscope. However, this is disadvantageous due to the major mechanical, thermal, and chemical stress on the pressure sensor, particularly during the sterilization of the medical instrument. Also, a miniature pressure sensor becomes necessary with such an arrangement. Such a miniature pressure sensor is relatively expensive. Moreover, a second medical instrument could be inserted only to measure the actual pressure in the cavity. But this would place added stress on the patient and also involve difficulty in handling. Additional sterilization measures would be necessary. Measuring uncertainty would also be very great, because an unnoticed blockage or leakage in the additional medical instrument could considerably distort the pressure measurement.

SUMMARY AND OBJECTS OF THE INVENTION

It is therefore the task of the invention to create a procedure for the perfusion of cavities of bodies of the customary type, and a device for executing the procedure, in which preselected, precisely measurable fluid pressure is created and is to be maintained in the body cavity, and in which the pressure in the body cavity is to be measured as precisely as possible.

The invention provides a method for the perfusion of body cavities with fluid supplied from a dispenser reservoir via a perfusion line and a medical instrument. The fluid is supplied by a pump and the arrangement includes a pressure sensor connected between the pump and the medical instrument and a control unit connected to the pressure sensor and connected to the pump. The method includes the steps of initiating perfusion of fluid via the perfusion line and the medical instrument and subsequently determining the pressure $P_{GEM}$ sensed by the pressure sensor and determining the volumetric flow of the fluid $\dot{V}$. The conductance of the fluid line and the medical instrument are determined prior to the perfusion such that during perfusion the control unit may determine the actual fluid pressure in the body cavity $P_{IST}$ based on $P_{GEM}$ $\dot{V}$ and the conductance of the line and medical instrument G. After the pressure is determined, the pressure may be maintained using the control unit by adjusting the volumetric rate of flow V based on the conductance G.

The apparatus of the invention includes the features described above with regard to the method wherein the control unit provides means for determining the actual fluid pressure in the body cavity $P_{IST}$ based on the pressure sensed at the pressure sensor $P_{GEM}$ less the volumetric rate of flow $V_{GEM}$ divided by the conductance G. The control unit also includes means for altering the pump to alter the volumetric rate of flow based on the pressure inside the body cavity $P_{IST}$.

According to the invention, the conductance of the perfusion line between the pressure sensor and the medical element, and the conductance of the instrument itself, are determined, and are used in the measuring procedure for the most precise determination of the actual pressure in the body cavity. The pressure in the body cavity can be measured with the greatest precision through continuous adjustment of the output of the pump with consideration of the determined conductance, and the pressure can be maintained constant at a predetermined value. The conductance is the reciprocal value of the flow resistance inside the perfusion line and inside the medical instrument. With the procedure according to the invention, the actual pressure in the body cavity can thereby be determined with the greatest precision without the help of a second medical instrument. This facilitates easy management of the procedure and the device working with the procedure with a high degree of security and great measurement reliability. With one and the same conductance of the hollow needle of the medical instrument, it is possible to work with a heavy flow without the expectation of measurement value uncertainties concerning the body cavity pressure because of the pressure drop in the hollow needle of the medical instrument. Also, self-monitoring is possible, since with a specific performance of the pump of the pressure at least the flow pressure must be indicated. With indication of the apparatus pressure in the perfusion line and the pressure reached in the body cavity, the conductance of the hollow needle of the medical instrument can be estimated.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

DESCRIPTION OF THE PREFERRED EMBODIMENT

Figure 1:
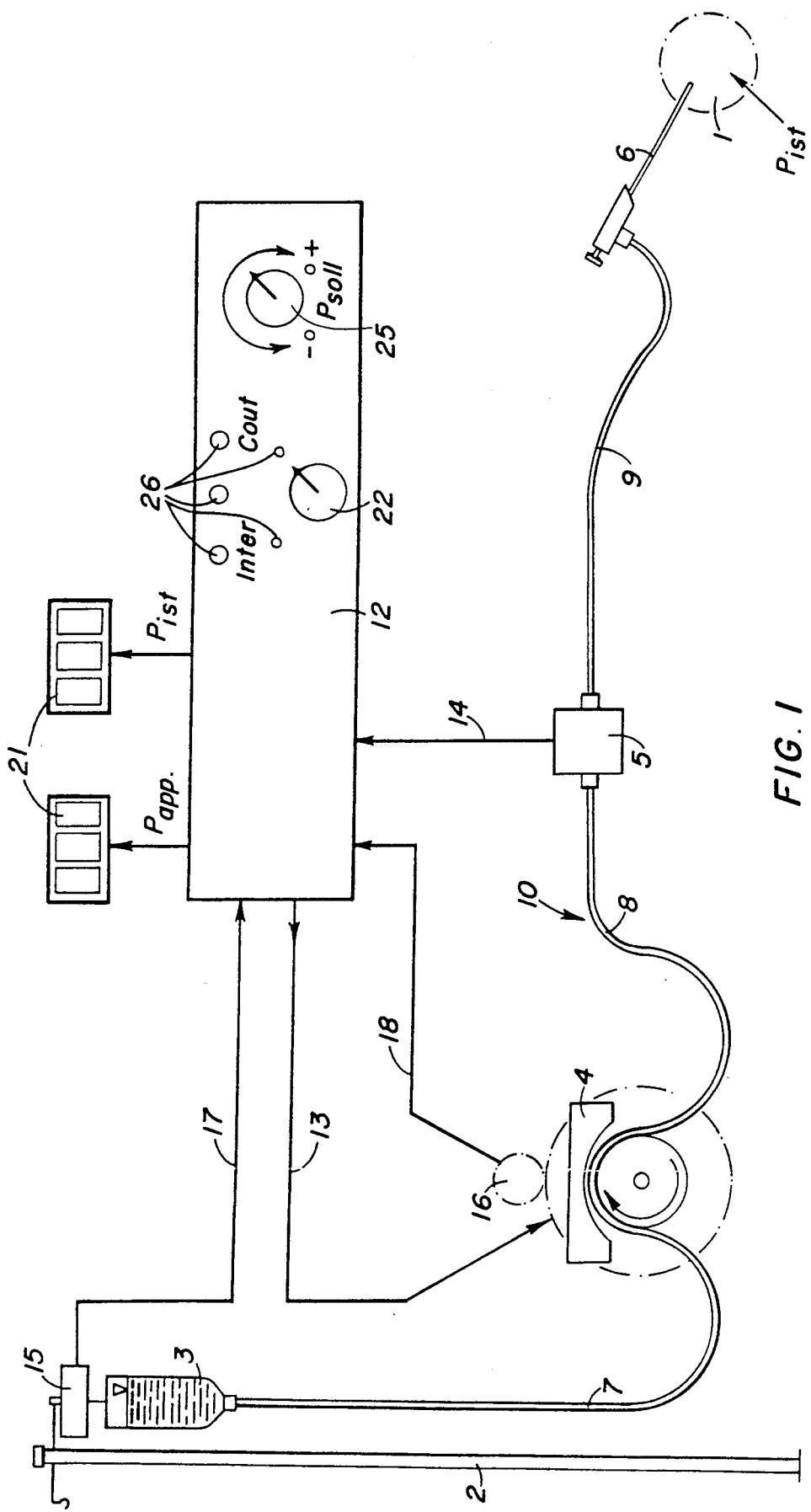
FIG. 1 is a schematic view of the device for carrying out the invention.

The device of the perfusion of body cavities 1 includes a dispenser reservoir 3 for a perfusion fluid, said dispenser reservoir 3 being suspended from a stand 2, a pump 4, constructed specifically as a peristaltic pump, a pressure sensor 5, a medical instrument 6, in particular an endoscope, such as, for example, an arthroscope, a perfusion line 10 consisting of hose lines 7, 8 and 9, and also an adjustment and electronic system 12, which is electrically connected via connection lines 13, 14 with pump 4 or pressure sensor 5 for conveyance of the measurement values. The dispenser reservoir 3 is suspended form stand 2 via a weight sensor 15 sensing the amount of fluid in the dispenser reservoir. A revolution-counting sensor 16 is installed on pump 4. Weight sensor 15 and counting sensor 16 are connected with the adjustment and measuring unit 12 via lines 17, 18, to transmit the measurement values.

Figure 2:
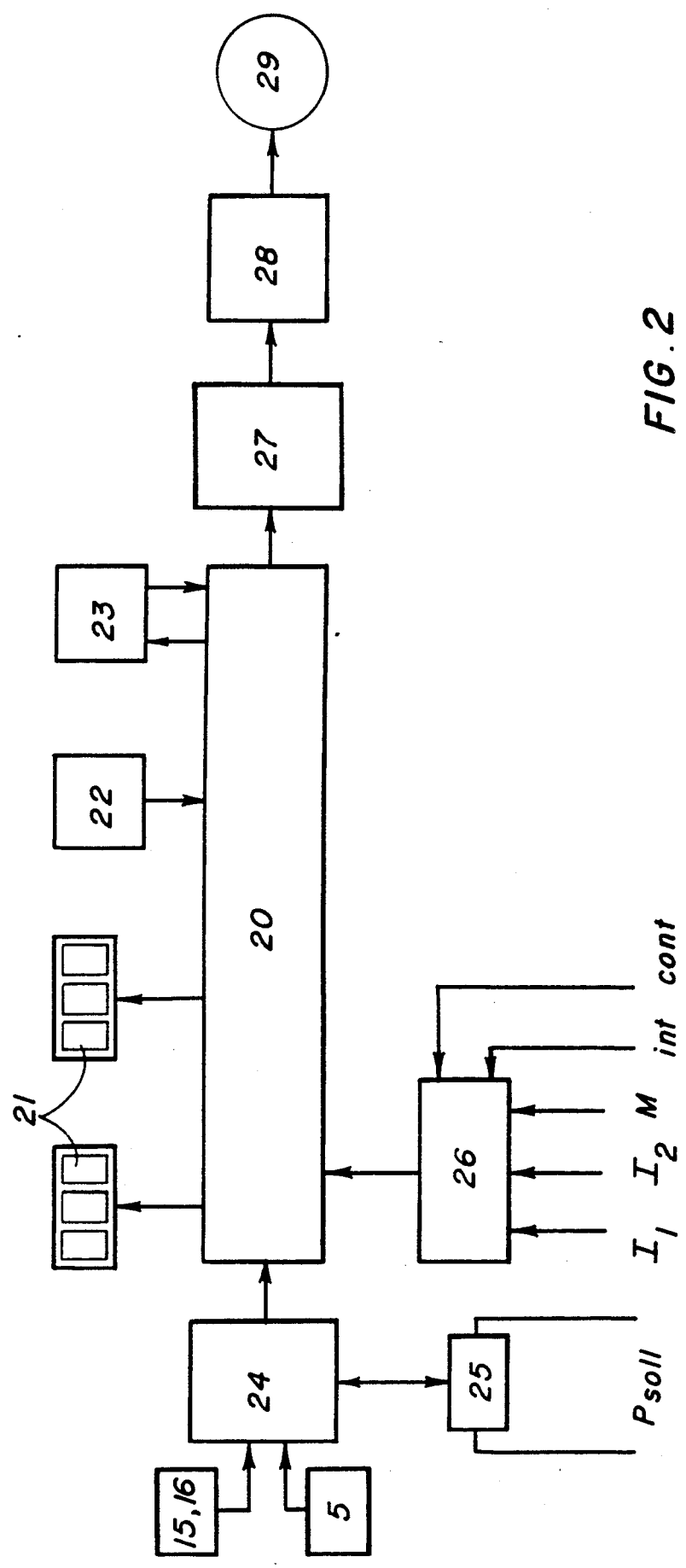
FIG. 2 is a block diagram of the adjustment and measuring unit of the device of the invention.

The adjustment and measuring unit 12, illustrated in greater detail in FIG. 2 as a block diagram, including a central processing unit (CPU) 20. LED indicators 21 are connected to CPU 20 for indicating the actual body cavity pressure $P_{IST}$ or the apparatus pressure $P_{APP}$. A program storage unit 22 and a data storage unit 23 are connected to the central processing unit 20. The values of the flow sensor 15 or 16 and the pressure sensor (pressure indicator) 5, as well as the target pressure $P_{SOLL}$ set are fed in via a potentiometer 24 of the adjustment and measuring unit 12. Either the weight sensor 15 on the dispenser reservoir 3 for the perfusion fluid or the counting sensor 16 on pump 4 is used as a flow sensor. Via a digital input and output area 26, the determined values I1, I2, M can be supplied as determined conductances of the perfusion line 9 between pressure sensor 5 and medical instrument 6 and of medical instrument 6 itself. Moreover, via the digital input-output area 26, control procedures—such as continuous perfusion (cont) and intermittent perfusion (int)—can be fed in. The determined conductances and the pre-determined values for the continuous or intermittent perfusion can be set by means of press-buttons installed on the front of adjustment and measurement unit 12. Also, the LED indicators 21 for the body cavity pressure $P_{IST}$ and apparatus pressure $P_{APP}$ are also located there. Lastly, program storage 22 and potentiometer 25 for inputting the target values $P_{SOLL}$ are also located on the front of the device.

Adjustment and measurement unit 12 controls motor 29 of pump 4 via a D/A converter 27 and an output stage 28.

Figure 3:
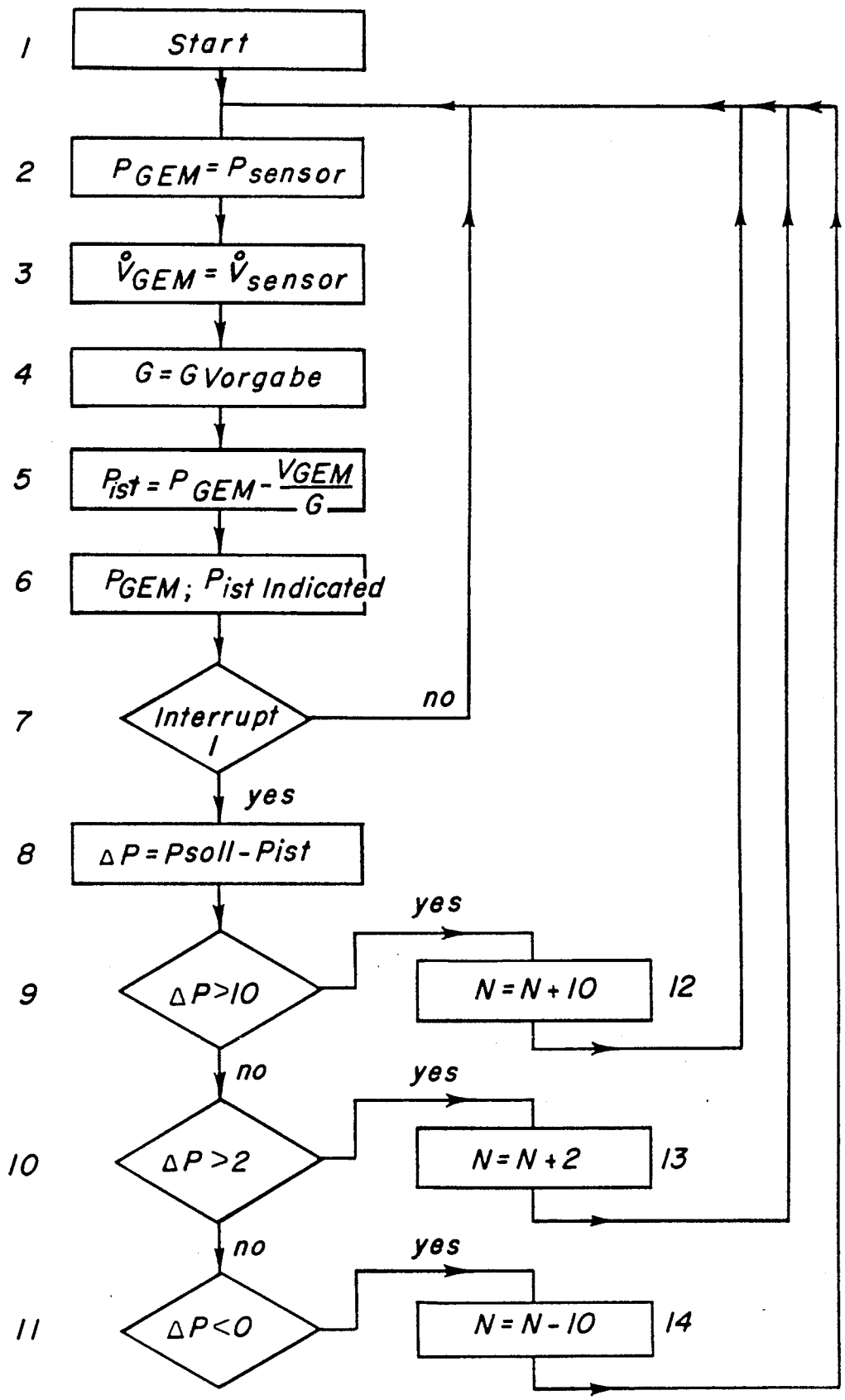
FIG. 3 shows the program flow chart of the adjustment and measuring unit.

The described device works according to the program flow chart of the adjustment and measuring unit 4, illustrated in simplified form in FIG. 3. After the triggering of the start-up impulse in stage 1, in stage 2 the pressure value measured by pressure sensor 5 is changed via the A/D converter 24 and is fed into the central computer unit 20 and is stored as pressure value $P_{GEM}$. In stage 3, flow value $\dot{V}_{SENSOR}$ is measured via flow sensors 15, 16 and is converted by A/D converter 24, and is stored as flow value $\dot{V}_{GEM}$. In stage 4, conductance G, determined against the atmosphere, of the medical instrument 6, as well as hose section 9, is determined, or conductance $G_{VORGABE}$ is is input or obtained from the previously selected storage locations $I_1$ $I_2$, or M via digital input-output areas 26 (i.e. conductance in formation for instruments and/or line is stored in memory areas and accessed at locations I, I or M). In stage 5, the actual body cavity pressure $P_{IST}$ is computed from the previously determined values according to the following formula:

$$P_{IST} = P_{GEM} - \frac{V_{GEM}}{G}$$

In stage 6, the computed body cavity pressure $P_{IST}$ and the measured apparatus pressure $P_{GEM}$ are indicated on the LED indicators 20.

In stage 7, the clock generator is queried for the pressure control trigger. If the result in stage 7 is "no", the program is switched back to stage 2. If the answer is "yes," stage 8 is reached.

In stage 8, the differential pressure $\Delta P$ is computed from the target pressure $P_{SOLL}$ and the actual pressure $P_{IST}$, using the following formula:

$$\Delta P = P_{SOLL} - P_{IST}$$

If in stage 9 a differential pressure $\Delta P$ of less than 10 results, the program flow chart is switched back to stage 2 via intermediate stage 12, in which process rpm N of pump 4 is increased to N=N+10. If the differential pressure $\Delta P$ is smaller than 20 but nevertheless >2, in stage 10 the program flow chart is switched back to stage 2 via intermediate stage 13, the rmp N of pump 4 being increased to N=N+2. If the differential pressure $\Delta P$ is ≧ 2, the switch is to stage 11, with rpm N of pump 4 being decreased to N=N−10. The program flow chart is switched back to stage 2 via intermediate stage 14. In the intermediate stages 12 to 14, by increasing or decreasing the rpm of pump 4, the volume flow V is increased or diminished, and the pressure in body cavity 1 is thereby maintained constantly at a preset value by means of continuous adjustment of the output of pump 4, with due consideration for the preset or computed conductances.

While specific embodiments of the invention have been shown and described in detail to illustrate the application of the principles of the invention, it will be understood that the invention may be embodied otherwise without departing from such principles.

We claim:

1. A method for the perfusion of body cavities with fluid supplied from a dispenser reservoir via a perfusion line and a medical instrument by a pump including a pressure sensor connected between the pump and the medical instrument and a control unit connected to the pressure sensor and connected to the pump, comprising the steps of:

determining the conductance of the fluid line between the pressure sensor and the medical instrument and determining the conductance of the medical instrument to provide the overall conductance G;

connecting the medical instrument to the body cavity of a patient;

initiating perfusion of fluid via the perfusion line and medical instrument;

determining the pressure $P_{GEM}$ sensed by the pressure sensor;

determining the volumetric rate of flow $\dot{V}$;

determining the actual fluid pressure in the body cavity $P_{IST}$ based on the pressure PGEM sensed, the volumetric rate of flow $\dot{V}$ and the overall conductance G; and attaining and maintaining the actual pressure $P_{IST}$ equal to a preset value of the volumetric rate of flow $\dot{V}$ through continuous adjustment of the volumetric rate of flow $\dot{V}$ based on the overall conductance G.

2. A method according to claim 1, further comprising the steps of:

determining the overall conductance G of the perfusion line between the sensor and the medical instrument and the overall conductance G of the medical instrument by initiating a test conveyance of fluid by the pump through the perfusion line and medical instrument against atmospheric pressure for a plurality of values of volumetric rate of flow $\dot{V}$ and storing the determined overall conductance G in a memory associated with said control unit.

3. A method according to claim 1, wherein the conductance G of various medical instruments are stored in advance in a memory associated with the control unit.

4. An apparatus for the perfusion of body cavities with a fluid, comprising:

a dispenser reservoir;

a perfusion line connected to said reservoir;

a medical instrument connected to said perfusion line at an opposite end from said dispenser reservoir;

pump means connected to said perfusion line;

a pressure sensor connected to said perfusion line between said pump means and said medical instrument; and control means, connected to said pump means and connected to said pressure sensor for determining the pressure $P_{GEM}$ sensed by the pressure sensor, for determining the volumetric flow of the fluid $\dot{V}$, or determining the conductance of the fluid line between the pressure sensor and the medical instrument and determining the conductance of the medical instrument to determine an overall conductance value G, for determining the actual fluid pressure in the body cavity $P_{IST}$ based on the pressure sensed $P_{GEM}$, the volumetric rate of flow $\dot{V}$ and the overall conductance G and for maintaining the pressure $P_{IST}$ equal to a present value $P_{SOLL}$ through continuous adjustment of the volumetric rate of flow V of the pump based on the conductance G.

5. A device according to claim 4, further comprising a weight sensor connected to said dispenser reservoir providing information of the amount of fluid in the dispenser reservoir to said control unit.

6. A device according to claim 4, further comprising a revolution per minute (rpm) counter connected to said pump means and connected to said control means for the determination of the volumetric rate of flow $\dot{V}$.

7. A device according to claim 4, further comprising a flow sensor positioned on the perfusion line and connected to said control means for determining the volumetric rate of flow $\dot{V}=0$.

8. A device according to claim 4, wherein said control means shuts down the pump means for a period of time subsequent to the perfusion of fluid to determine the static pressure $P_{IST}$ corresponding to the actual cavity pressure, said control means comparing said static pressure $P_{IST}$ to the determined actual fluid pressure in the body cavity $P_{IST}$.

9. A device according to claim 4, wherein said control means includes LED indicators indicating the body cavity pressure $P_{IST}$ and an apparatus pressure $P_{APP}$.

10. A device according to claim 4, wherein said pump means is a pressure collar controlling gravitational flow of fluid from said dispenser reservoir.

11. A device according to claim 4, wherein said pump means is a fluid flow valve controlling gravitational flow of fluid from said dispenser reservoir.

12. A device according to claim 4, wherein said pump means is a peristaltic pump engaging the exterior of said perfusion line.

* * * * *